United States Patent [19]
Nelson

[11] Patent Number: 5,981,805
[45] Date of Patent: Nov. 9, 1999

[54] PEROXIDES

[75] Inventor: Fredrick F. Nelson, Landenberg, Pa.

[73] Assignee: Hercules Incorporated, Wilmington, Del.

[21] Appl. No.: 08/893,693

[22] Filed: Jul. 11, 1997

Related U.S. Application Data

[60] Provisional application No. 60/021,630, Jul. 12, 1996, and provisional application No. 60/032,345, Dec. 4, 1996.

[51] Int. Cl.⁶ .................................................. C07C 49/00
[52] U.S. Cl. ................. 568/561; 252/182.23; 525/333.8; 525/387
[58] Field of Search ........................ 568/561; 252/182.23

[56] References Cited

U.S. PATENT DOCUMENTS

| | | | |
|---|---|---|---|
| 2,668,180 | 2/1954 | Boardman | 260/610 |
| 3,658,914 | 4/1972 | Gregory | 568/561 |
| 3,787,504 | 1/1974 | Peri et al. | 260/610 |
| 3,919,326 | 11/1975 | Gregory | 568/561 |
| 4,202,790 | 5/1980 | Steller | 252/186 |
| 4,450,302 | 5/1984 | Willis | 502/150 |

FOREIGN PATENT DOCUMENTS

| | | |
|---|---|---|
| 0101175A | 2/1984 | European Pat. Off. . |
| 2053234 | 2/1981 | United Kingdom . |

*Primary Examiner*—Bernard Lipman
*Attorney, Agent, or Firm*—Robert P. O'Flynn O'Brien

[57] ABSTRACT

Blends of meta and para isomers of α, α'-bis(t-butylperoxy) diisopropylbenzene are disclosed as well as methods of producing blends of α, α'-bis(t-butylperoxy) diisopropylbenzene with desired ratios of meta and para isomers.

Additionally, blends of meta and para isomers of α, α'-bis(t-butylperoxy) diisopropylbenzene and tertiary alkyl cumyl peroxides are disclosed.

The peroxides are useful for absorbing in polymers and subsequently crosslinking the polymers. The peroxide blends may be adjusted to have melt points below temperatures at which the polymers become difficult to process during the absorption step because of stickiness.

21 Claims, 1 Drawing Sheet

PEROXIDES

This application claims benefit of provisional application Ser. No. 60/021,630 filed Jul. 12, 1996, and claims benefit of provisional applicant Ser. No. 60/032,345 filed Dec. 4, 1996.

FIELD OF THE INVENTION

This invention relates to polyperoxides, particularly blends of meta and para isomers of α, α'-bis(t-butylperoxy) diisopropylbenzene and a method of producing blends of meta and para isomers of α, α'-bis(t-butylperoxy) diisopropylbenzene with desired ratios.

This invention additionally relates to blends of meta and para isomers of α, α'-bis(t-butylperoxy) diisopropylbenzene and tertiary alkyl cumyl peroxides.

BACKGROUND OF THE INVENTION

Polyperoxides are used in industry for cross linking polymers. Among the polyperoxides which have been used in cross linking polymers is α, α'-bis(t-butylperoxy) diisopropylbenzene. The α, α'-bis(t-butylperoxy) diisopropylbenzene has been available as a blend of the meta and para isomers where the ratio of meta to para isomers is about 2.0/1 and where the meta isomer constitutes about 68% of the blend and the para isomer constitutes about 32% of the blend. This blend, available from Hercules Incorporated, Wilmington, Del. as Vul-Cup® organic peroxide, is produced by a process as disclosed in U.S. Pat. No. 3,658,914 incorporated herein in its entirety, using di-isopropyl benzene as a starting material.

Generally, the isomer ratio of the polyperoxide is determined by the process of alkylating cumene. This process results in a meta to para isomer ratio of about 2:1.

Also, α, α'-bis(t-butylperoxy) diisopropylbenzene is available either in its pure meta or para form.

While these blends are useful in the cross linking of polymers, the temperature range over which these materials melt sometimes interferes with absorption of the liquid peroxide into the polymers. If the α, α'-bis(t-butylperoxy) diisopropylbenzene melts near the softening point of a polymer to be cross linked, problems frequently arise due to polymer particles sticking together during the absorption process. This is a problem with the available 2/1 blend as well as with nearly pure meta or para isomers.

It has been discovered that by selecting certain ratios of the meta and para isomers in the polyperoxide, polyperoxides having lower melt point ranges may be obtained. These polyperoxides may be produced either through selecting the desired ratio of di-isopropyl benzene as a starting material if that material is to be oxidized to its corresponding diol form or selecting di-isopropyl benzene diol with the desired isomeric ratio or through blending of meta and para isomers of the polyperoxide.

A need exists for peroxides which melt at a lower temperature than the polyperoxides described hereinabove. U.S. Pat. No. 4,450,302 discloses peroxide blends that have low melting points and which are useful in the crosslinking of polymers such as polyethylene, EPDM and copolymers of ethylene and vinyl acetate. However, these peroxide blends exhibit high volatility and poor scorch resistance. Scorch is known in the art as premature crosslinking of a polymer system prior to forming the polymer into desirable shapes. Poor scorch resistance of the peroxide blends of U.S. Pat. No. 4,450,302 is as a result of these peroxide blends containing dicumyl peroxide which has a scorch initiation temperature approximately 10° C. below the scorch initiation temperature of the inventive peroxides blends and polyperoxides.

The peroxide blends of U.S. Pat. No. 4,450,302 discloses high amounts of t-butyl cumyl peroxide. T-butyl cumyl peroxide is a relatively volatile material and has a vapor pressure of 20 mm Hg at ambient temperature. The vapor pressure of the α, α'-bis(t-butylperoxy) diisopropylbenzene is essentially 0 mm Hg at ambient temperature. It is desirable to minimize the volatility of peroxides used in crosslinking polymers because peroxide loss from polymer/peroxide blends effects the manner in which the polymer cures.

SUMMARY OF THE INVENTION

The invention relates to a polyperoxide comprising, α, α'-bis(t-butylperoxy) diisopropylbenzene, wherein the α, α'-bis(t-butylperoxy) diisopropylbenzene comprises a blend of less than about 32% and greater than about 0% para isomer and greater than 68% and less than about 100% meta isomer.

Additionally, the invention relates to polyperoxide blends which exhibit a Clear Point below 53° C., preferably a Clear Point below about 45° C., more preferably a Clear Point about 44° C.

Peroxides of the invention are useful in cross linking polymers selected from the group consisting of natural rubber, polyethylene, polyisoprene, polybutadiene, copolymers of ethylene and other olefins with three to twelve carbon atoms. Additionally small amounts of dienes may be added as in EPDM. Other useful monomers include vinyl acetate, acrylonitrile, ethyl acrylate and other acrylates containing up to 14 carbon atoms.

Polyperoxides of the invention may be produced by a process comprising the steps of blending para and meta isomers of di-isopropyl benzene to obtain a blend of less than about 32% and greater than about 0% para isomer and greater than about 68% and less than about 100% meta isomer and then oxidizing the blend to form the corresponding diol, and reacting the diol with t-butyl hydroperoxide to form the polyperoxide.

Polyperoxides of the invention may also be produced by blending para and meta isomers of di-isopropyl benzene diol to obtain a blend of less than about 32% and greater than about 0% para isomer and greater than about 68% and less than about 100% meta isomer, and reacting the diol with t-butyl hydroperoxide to form the polyperoxide.

Alternatively, polyperoxides of the invention may be produced by obtaining para and meta isomers of α, α'-bis(t-butylperoxy) diisopropylbenzene, and blending the isomers to obtain a blend of less than about 32% and greater than about 0% para isomer and greater than about 68% and less than about 100% meta isomer.

Additionally, the invention relates to blends of para and meta isomers of α, α'-bis(t-butylperoxy) diisopropylbenzene and tertiary alkyl cumyl peroxides wherein the α, α'-bis(t-butylperoxy) diisopropylbenzene comprises from about 95% to about 5% by weight and the tertiary alkyl cumyl peroxides comprises from about 5% to about 95% by weight of the blend. Preferably, the α, α'-bis(t-butylperoxy) diisopropylbenzene comprises from about 50% to about 5% by weight and the tertiary alkyl cumyl peroxides comprises from about 50% to about 95% by weight of the blend, more preferably, α, α'-bis(t-butylperoxy) diisopropylbenzene comprises from about 90% to about 70% by weight and the tertiary alkyl cumyl peroxides comprises from about 10% to about 30% by weight of the blend.

The tertiary alkyl cumyl peroxide has the formula:

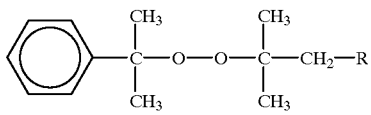

where R may be either hydrogen, or an alkyl group from C1 to C5.

The tertiary alkyl cumyl peroxides may be selected from the group consisting of t-butyl cumyl peroxide and t-amyl cumyl peroxide. Preferably, the tertiary alkyl cumyl peroxide comprises t-butyl cumyl peroxide.

DETAILED DESCRIPTION OF THE INVENTION

Figure 1:
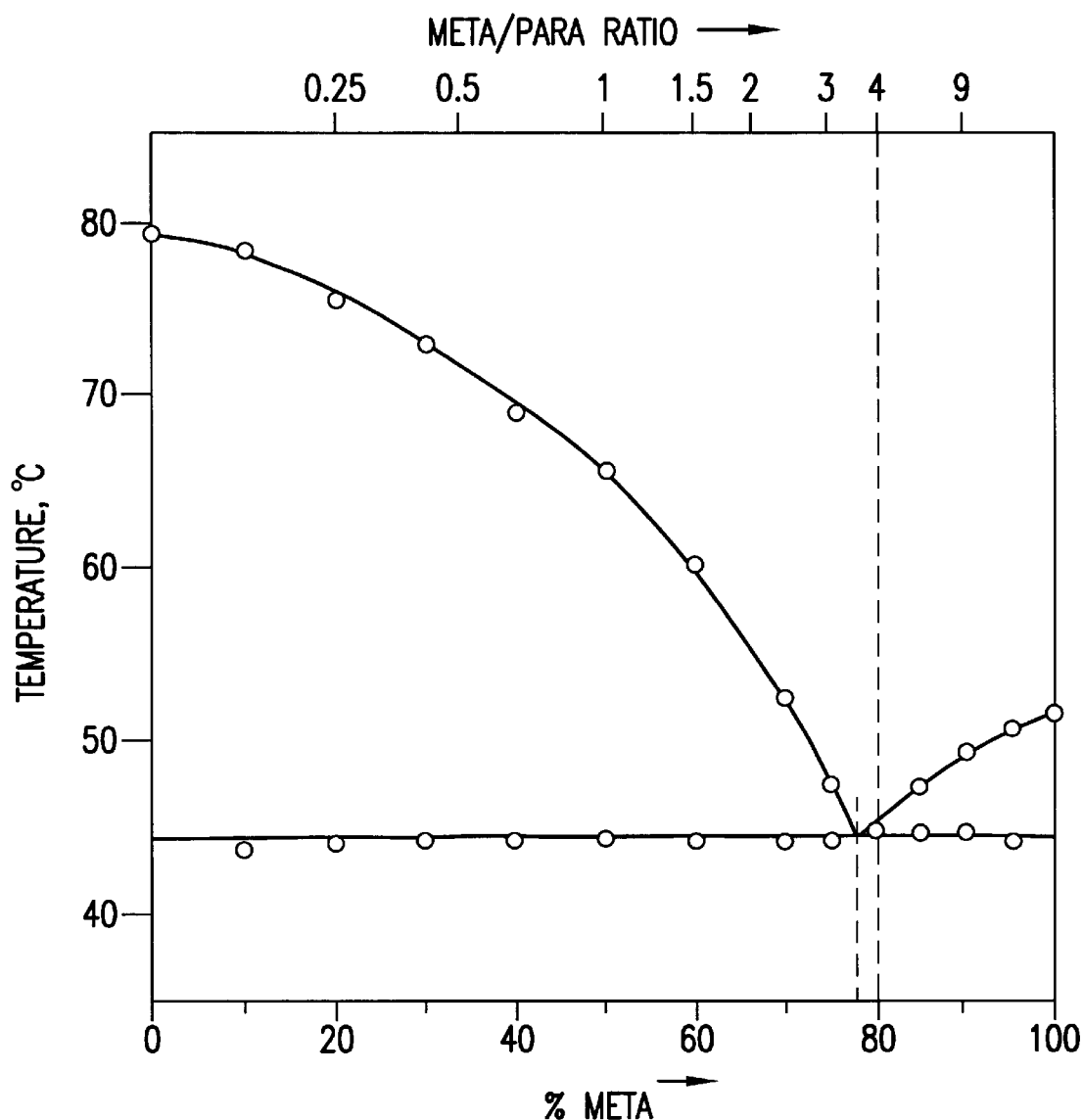
FIG. 1 is a phase diagram of the ratio of the meta to para isomers of α, α'-bis(t-butylperoxy) diisopropylbenzene. Composition is plotted versus the Clear Point temperature in degrees Celsius. From this diagram, the eutectic point of the blend of meta to para isomers can be estimated.

The polyperoxides of the invention may be produced using the process disclosed in U.S. Pat. No. 3,658,914, previously incorporated hereinabove by reference.

Di-isopropyl benzene ("DIB") which may be used as a starting material in the production of the polyperoxides of the invention may be obtained in both the meta and para isomers (available from Eastman Chemical Company, Kingsport, Tenn.). This permits one to produce any ratio of the meta and para isomers. DIB is obtained in a desired meta/para ratio for the final polyperoxide prior to its subsequent reaction. The dialcohol derivatives of the DIB are commercially available and also can be used as starting materials. The peroxide blends of the invention also can be made by blending mixtures of α, α'-bis(t-butylperoxy) diisopropylbenzene.

In polyperoxides of the invention, the ratio of the meta to para isomers is greater than about 2/1 and less than about 10/1 more preferably between about 2.3/1 and about 8/1 and most preferably about 3.5/1. The amount of para isomer is less than about 32% and greater than about 0% while the amount of meta isomer is greater than about 68% and less than about 100%, more preferably the amount of para isomer is less than about 30% and greater than about 0% and the meta isomer is greater than about 70% and less than about 100%, most preferably the amount of para isomer is about 22% and the amount of the meta isomer is about 78%. All parts and percentages listed herein are by weight unless otherwise noted.

The polyperoxides of the invention have lower melting ranges, as determined by the method outlined hereinbelow, when compared to conventional polyperoxide blends. It is acknowledged that solvents, impurities or other materials will lower the melting points of peroxides.

The melting ranges of the peroxides are determined using the following method. A one (1) inch diameter test tube is filled approximately one half (½) full with approximately twenty (20) grams of melted peroxide. A thermometer is inserted into the peroxide. The peroxide is subsequently allowed to cool slowly. As the sample cools, a point is reached at which the sample becomes hazy. This is called the "Haze Point". The sample is continued to be cooled until the liquid column in the thermometer can no longer be seen when the thermometer is at the back side of the test tube. This point is called the "Cloud Point".

Once the peroxide has solidified and the Cloud Point has been reached, the test tube is placed in a water bath and slowly warmed. The temperature at which the liquid peroxide is no longer hazy is observed and noted. This is known as the "Haze Free Point". Heating of the test tube is continued until no solid peroxide crystals are observed in the test tube. This is known as the "Clear Point". Each sample is run through this cycle at least three times. The results of the first cycle are ignored. Results for the next two cycles should agree to within about 1° C. in order to be used.

Referring to FIG. 1, a phase diagram of the ratio of the blend of meta to para isomers of α, α'-bis(t-butylperoxy) diisopropylbenzene versus the Clear Point temperature in degrees Celsius is plotted. From this diagram, the eutectic point of the blend of meta to para isomers can be estimated.

Polyperoxides of the invention exhibit Clear Points of below 53° C., more preferably below about 45° C., most preferably about 44° C. Additionally, polyperoxides of the invention exhibit Haze Free Points of below 39° C., more preferably below about 30° C., most preferably about 29° C.

Polyperoxides of the invention exhibit Clear Points of below 53° C. and Haze Free Points of below 39° C. more preferably Clear Points below about 45° C. and Haze Free Points of below about 30° C., most preferably Clear Points of about 44° C. and Haze Free Points of about 29° C.

Additionally, the invention relates to blends of para and meta isomers of α, α'-bis(t-butylperoxy) diisopropylbenzene and tertiary alkyl cumyl peroxides wherein the α, α'-bis(t-butylperoxy) diisopropylbenzene comprises from about 95% to about 5% by weight and the tertiary alkyl cumyl peroxides comprises from about 5% to about 95% by weight of the blend. Preferably, the α, α'-bis(t-butylperoxy) diisopropylbenzene comprises from about 50% to about 5% by weight and the tertiary alkyl cumyl peroxides comprises from about 50% to about 95% by weight of the blend, more preferably, α, α'-bis(t-butylperoxy) diisopropylbenzene comprises from about 90% to about 70% by weight and the tertiary alkyl cumyl peroxides comprises from about 10% to about 30% by weight of the blend.

Tertiary alkyl cumyl peroxides are well known in the art as are the methods for its preparation. These peroxides have the formula:

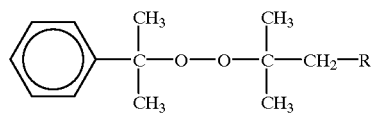

where R may be either hydrogen, or an alkyl group from C1 to C5.

The tertiary alkyl cumyl peroxides may be selected from the group consisting of t-butyl cumyl peroxide and t-amyl cumyl peroxide. Preferably, the tertiary alkyl cumyl peroxide comprises t-butyl cumyl peroxide.

T-butyl cumyl peroxide also referred to as α, α-dimethylbenzyl t-buty peroxide, has a melting point of about 15.5° C. It may be prepared in accordance with the teachings of U.S. Pat. No. 2,668,180, incorporated herein by reference in its entirety.

T-butyl cumyl peroxide is available in purities of from about 90% to 100%. Impurities present, if any, will include cumene hydroperoxide, α, α-dimethylbenzyl alcohol, t-butyl hydroperoxide, acetophenone, and α-methylstyrene.

T-butyl cumyl peroxide is available from Hercules Incorporated as Peroxide D-16® peroxide.

The polyperoxides and the blends of para and meta isomers of α, α'-bis(t-butylperoxy) diisopropylbenzene and tertiary alkyl cumyl peroxide of the invention are useful as cross linking agents for use with various polymers. The polyperoxides and the blends of para and meta isomers of α, α'-bis(t-butylperoxy) diisopropylbenzene and tertiary alkyl cumyl peroxide are particularly useful in cross-linking olefinic polymers. Among the polymers which may be cured with the polyperoxides and the blends of para and meta isomers of α, α'-bis(t-butylperoxy) diisopropylbenzene and tertiary alkyl cumyl peroxide of the invention are polymers selected from the group consisting of natural rubber, polyethylene, polyisoprene, polybutadiene copolymers of ethylene and other olefins with three to twelve carbon atoms. Additionally small amounts of dienes may be added as in EPDM. Other useful monomers include vinyl acetate, acrylonitrile, ethyl acrylate and other acrylates containing up to 14 carbon atoms.

The following examples serve to further illustrate the invention, parts and percentages being by weight unless otherwise indicated.

EXAMPLES

Example 1

An example of polyperoxide was produced in the following manner. A mixture of 22% para and 78% meta di-isopropyl benzene was obtained (Eastman Chemical Company, Kingsport, Tenn.). The mixture was oxidized to produce the corresponding diols. The diols were reacted with t-butyl hydroperoxide to form the polyperoxide.

A comparative example was produced using 32% para and 68% meta di-isopropyl benzene obtained (Eastman Chemical Company, Kingsport, Tenn.) rather than the 22% para and 78% meta ratio of the example.

Properties of the example and comparative example are as follows:

| Sample | % para by weight | % meta by weight | Haze Point | Cloud Point | Haze Free Point | Clear Point |
|---|---|---|---|---|---|---|
| Comparative Example | 32 | 68 | 46.3° C. | 44.8° C. | 53.0° C. | 53.8° C. |
| Example 1 | 22 | 78 | 36.8° C. | 35.8° C. | 43.3° C. | 44.0° C. |

This example demonstrates the reduction in the Haze Point, Cloud Point, Haze Free Point and Clear Point of the polyperoxide of the invention when compared to the values of the Comparative Example.

Example 2

An example of polyperoxide blends was produced in the following manner. A peroxide comprising a blend of isomers similar to example 1 was obtained. To this blend, various amounts of t-butyl cumyl peroxide ("TBCP") were added and the Haze Point, Cloud Point, Haze Free Point and Clear Point of the mixtures were measured. The results of this testing are found in the following table.

| Sample | Bis Peroxide[a], wt % | TBCP[b], wt % | Haze Point, ° C. | Cloud Point, ° C. | Haze Free Point, ° C. | Clear Point, ° C. |
|---|---|---|---|---|---|---|
| Ex. 1 | 100 | 0 | 36.8 | 36.3 | 42.5 | 43.5 |
| Ex. 2-a | 90 | 10 | 37.0 | 31.8 | 38.5 | 39.3 |
| Ex. 2-b | 80 | 20 | 28.5 | 24.8 | 35.8 | 36.8 |
| Ex. 2-c | 70 | 30 | 22.8 | 18.8 | 31.0 | 32.3 |
| Ex. 2-d | 60 | 40 | 16.8 | 14.8 | 24.5 | 25.3 |
| Ex. 2-e | 50 | 50 | 8.5 | 3.3 | 19.3 | 20.3 |

[a]Bis Peroxide comprised a blend of 22% para and 78% meta isomers of α,α'-bis(t-butylperoxy) diisopropylbenzene by weight.
[b]TBCP used was Peroxide D-16 ® peroxide, (available from Hercules Incorporated).

The above results clearly demonstrate that the addition of TBCP to the peroxide blends of the invention result in a further depression of the Haze Point, Cloud Point, Haze Free Point and Clear Point of the materials.

It is not intended that the examples given herein should be construed to limit the invention, but rather they are submitted to illustrate some of the specific embodiments of the invention. Various modifications and variations of the present invention can be made without departing from the scope of the appended claims.

I claim:

1. A polyperoxide comprising,
   α, α'-bis(t-butylperoxy) diisopropylbenzene, wherein the α, α'-bis(t-butylperoxy) diisopropylbenzene comprises a blend of less than about 32% and greater than 0% para isomer and greater than 68% and less than about 100% meta isomer, wherein the blend exhibits a Clear Point below 53° C.

2. The polyperoxide of claim 1, wherein the α, α'-bis(t-butylperoxy) diisopropylbenzene comprises a blend of less than about 30% and greater than about 0% para isomer and greater than about 70% and less than about 100% meta isomer.

3. The polyperoxide of claim 2, wherein the α, α'-bis(t-butylperoxy) diisopropylbenzene comprises a blend of about 22% para isomer and about 78% meta isomer.

4. The polyperoxide of claim 1, wherein the blend exhibits a Clear Point below about 45° C.

5. The polyperoxide of claim 4, wherein the blend exhibits a Clear Point about 44° C.

6. A process for producing a polyperoxide comprising the steps of:

blending para and meta isomers of di-isopropyl benzene to obtain a blend of less than about 32% and greater than 0% para isomer and greater than 68% and less than about 100% meta isomer, oxidizing the blend to form the corresponding diol, and reacting the diol with t-butyl hydroperoxide to form the polyperoxide isomer, wherein the blend exhibits a Clear Point below 53° C.

7. A process for producing a polyperoxide comprising the steps of:
blending para and meta isomers of di-isopropyl benzene diol to obtain a blend of less than about 32% and greater than 0% para isomer and
greater than 68% and less than about 100% meta isomer, and reacting the diol with t-butyl hydroperoxide to form the polyperoxide, wherein the blend exhibits a Clear Point below 53° C.

8. A process for producing a polyperoxide comprising the steps of:
obtaining para and meta isomers of α, α'-bis(t-butylperoxy) diisopropylbenzene, and
blending the isomers to obtain a blend of less than about 32% and greater than 0% para isomer and greater than 68% and less than about 100% meta isomer, wherein the blend exhibits a Clear Point below 53° C.

9. A polyperoxide comprising,
α, α'-bis(t-butylperoxy) diisopropylbenzene, wherein the α, α'-bis(t-butylperoxy) diisopropylbenzene comprises a blend having a ratio of meta to para isomers greater than 2/1 and less than 10/1, wherein the blend exhibits a Clear Point below 53° C.

10. The polyperoxide of claim 9, wherein the α, α'-bis(t-butylperoxy) diisopropylbenzene comprises a blend having a ratio of meta to para isomers between about 2.3/1 and about 8/1.

11. The polyperoxide of claim 10, wherein the α, α'-bis(t-butylperoxy) diisopropylbenzene comprises a blend having a ratio of meta to para isomers of about 3.5/1.

12. A peroxide blend comprising,
(a) 5% to about 95% by weight tertiary alkyl cumyl peroxide, and
(b) 95% to about 5% by weight a polyperoxide comprising α, α'-bis(t-butylperoxy) diisopropylbenzene, wherein the α, α'-bis(t-butylperoxy) diisopropylbenzene comprises a blend of less than about 32% and greater than 0% para isomer and greater than 68% and less than about 100% meta isomer, wherein the blend exhibits a Clear Point below 53° C.

13. The peroxide blend of claim 12, wherein the α, α'-bis(t-butylperoxy) diisopropylbenzene comprises a blend of less than about 30% and greater than about 0% para isomer and greater than about 70% and less than about 100% meta isomer.

14. The peroxide blend of claim 13, wherein the α, α'-bis(t-butylperoxy) diisopropylbenzene comprises a blend of about 22% para isomer and about 78% meta isomer.

15. The peroxide blend of claim 13, wherein the blend exhibits a Clear Point below about 45° C.

16. The peroxide blend of claim 14, wherein the blend exhibits a Clear Point about 44° C.

17. The peroxide blend of claim 12, wherein the blend comprises (a) 50% to about 95% by weight tertiary alkyl cumyl peroxide, and (b) 50% to about 5% by weight by weight a polyperoxide comprising α, α'-bis(t-butylperoxy) diisopropylbenzene.

18. The peroxide blend of claim 17, wherein the blend comprises (a) 10% to about 30% by weight tertiary alkyl cumyl peroxide, and (b) 90% to about 70% by weight a polyperoxide comprising α, α'-bis(t-butylperoxy) diisopropylbenzene.

19. The peroxide blend of claim 12, wherein the tertiary alkyl cumyl peroxide has the formula:

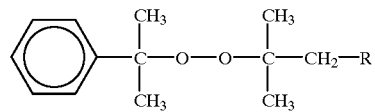

where R may be either hydrogen, or an alkyl group from C1 to C5.

20. The peroxide blend of claim 19, wherein the tertiary alkyl cumyl peroxide is selected from the group consisting of t-butyl cumyl peroxide and t-amyl cumyl peroxide.

21. The peroxide blend of claim 20, wherein the tertiary alkyl cumyl peroxide comprises-t-butyl cumyl peroxide.

* * * * *